United States Patent [19]
Kubota

[11] Patent Number: 5,834,007
[45] Date of Patent: Nov. 10, 1998

[54] WOUND-COVERING MATERIAL AND WOUND-COVERING COMPOSITION

[75] Inventor: Sunao Kubota, Tokyo, Japan

[73] Assignee: Ogita Biomaterial Laboratories Co. Ltd., Toyama, Japan

[21] Appl. No.: 617,921

[22] PCT Filed: Sep. 16, 1994

[86] PCT No.: PCT/JP94/01524

§ 371 Date: Mar. 5, 1996

§ 102(e) Date: Mar. 5, 1996

[87] PCT Pub. No.: WO95/07719

PCT Pub. Date: Mar. 23, 1995

[30] Foreign Application Priority Data

Sep. 16, 1993 [JP] Japan .................................. 5-253703

[51] Int. Cl.$^6$ .................. A61F 2/00; A61L 15/00
[52] U.S. Cl. .......................... 424/443; 424/445
[58] Field of Search .................... 424/423, 443, 424/445; 602/48, 49, 52, 58; 604/304, 336

[56] References Cited

U.S. PATENT DOCUMENTS

| | | | |
|---|---|---|---|
| 4,188,373 | 2/1980 | Krezanoski | 424/78 |
| 5,346,703 | 9/1994 | Viegas et al. | 424/486 |
| 5,395,305 | 3/1995 | Koide et al. | 602/48 |
| 5,505,952 | 4/1996 | Jiang et al. | 424/423 |

FOREIGN PATENT DOCUMENTS

| | | |
|---|---|---|
| 386960 | 9/1990 | European Pat. Off. . |
| 64-223181 | 4/1991 | Japan . |
| 5255119 | 10/1993 | Japan . |
| 5262882 | 10/1993 | Japan . |
| 6245988 | 9/1994 | Japan . |

OTHER PUBLICATIONS

"The Sol–Gel Transition and the Liquid–Liquid Phase Separation in Poly (vinyl chloride) Solutions", Kawanishi et al., *Polymer Journal*, vol. 18, No. 5, pp. 411–416 (1986).

"A Synthetic Hydrogel with Thermoreverisible Gelation. I. Preparation and Rheological Properties", Yoshioka et al., J.M.S., *Pure Appl. Chem.*, A31(1), pp. 113–120 (1994).

"A Synthetic Hydrogel with Thermoreverisible Gelation. II. Effect of Added Salts", Yoshioka et al., J.M.S., *Pure Appl. Chem.*, A31(1), pp. 121–125 (1994).

"Preparation of Poly (n–isopropylacrylamide)—b–Poly (ethylene Glycol) and Calorimetric Analysis of its Aqueous Solution", Yoshioka et al., J.M.S., *Pure Appl. Chem*, A31 (1), 109–112 (1994).

"Thermal Gelation Properties of Methyl and Hydroxypropyl Methylcellulose", N. Sarkar, *Journal of Applied Polymer Science*, vol. 24, pp. 1073–1087 (1979).

(List continued on next page.)

*Primary Examiner*—Thurman K. Page
*Assistant Examiner*—Kathryne E. Shelborne
*Attorney, Agent, or Firm*—Leydig, Voit & Mayer

[57] ABSTRACT

A wound-covering material is provided which includes at least a polymer having a sol-gel transition temperature in an aqueous solution, shows a substantial water-insolubility at a temperature higher than the sol-gel transition temperature, and shows a reversible water-solubility at a temperature lower than the sol-gel transition temperature. Such a wound-covering material may closely be attached to a wound surface having a complex profile, since it may be placed on the wound surface in a liquid state. In addition, the wound-covering material may provide a wound-covering matter which may rapidly be converted into a gel state due to the temperature of the wound so as to be closely attached to the wound surface and is stably attached to the wound surface in close contact. The resultant covering matter is stable without being dissolved by exudate secreted from the wound surface and may prevent the secretion of the exudate until the completion of the wound surface healing so as to promote the process of wound healing.

17 Claims, 7 Drawing Sheets

OTHER PUBLICATIONS

"Pluronic F–127 get preparation as an artificial skin in the treatment of third–degree burns in pigs", Nalbandian et al., *Journal of Biomed. Materials Research*, vol. 21, 1135–1148 (1987).

"Chitosan Derivatives Bearing $C_{10}$ Alkyl Glycoside Branches: A Temperature–Induced Gelling Polysaccharide", Holme et al., *Macromolecules* 1991, 24, pp. 3828–3833.

"A Synthetic Hydrogel with Thermoreversible Gelation, III: an NMR Study of the Sol–Gel Transition", *Polymers for Advanced Technologies*, Yoshioka et al., vol. 5, pp. 122–127.

WOUND-COVERING MATERIAL AND WOUND-COVERING COMPOSITION

TECHNICAL FIELD

The present invention relates to a wound-covering material which is suitably usable for a wound of an animal (inclusive of a human being), such as a burn and a bedsore. Further, the present invention relates to a wound-covering material which may be left stably standing on a wound for a long period of time; is capable of preventing exudation; and is capable of healing the wound without the necessity of exchange, even when the wound-covering material is kept under a condition such that it is closely attached or adhere to the surface of the wound. Further, the present invention relates to a wound-covering material having an analgesic function. Further, the present invention relates to a wound-covering material which is capable of healing a wound without the necessity of the implantation of skin, even when the wound to be healed is a wide-range full-thickness skin wound. Further, the present invention relates to a wound-covering material which is capable of promoting the healing of a wound while simultaneously preventing the infection of the wound. Furthermore, the present invention relates to a wound-covering composition which comprises, at least, water and the above-mentioned wound-covering material, and also to a wound-covering medium which includes a layer comprising the above-mentioned composition, and a low-water vapor-transmissive film disposed on the composition layer.

BACKGROUND ART

In various animals inclusive of human beings, it is considered that their skin has functions or roles of: (1) a barrier against stimuli (externally imparted to a living organism); and (2) the prevention of the escape of body fluid and protection of internal organs. When the tissue of the above-mentioned animal skin is damaged due to a wound such as a burn or a bedsore, it is necessary to temporarily cause a skin substitute to perform the above-mentioned functions of the normal skin.

Heretofore, there have been developed various wound-covering media which have a function of substituting for the skin functions until the wound is healed. Such wound-covering media may roughly be classified into the following types by the structures thereof:

(1) media having a structure containing pores communicating with each other, which are represented by woven fabric such as gauze, nonwoven fabric, or sponge, etc.

(2) Films which have been formed from synthetic polymers such as polyurethane and silicone rubber, or from materials produced by (or derived from) living organisms such as chitin, collagen and fibrin; and also have a structure having a very poor porosity.

(3) media comprising fine hydrogel particulates of a water-absorptive material.

(4) media having a composite structure which has been provided by combining the above-mentioned various kinds of structures.

From the viewpoint of substitution for skin functions, the above-mentioned various structures have both advantages and disadvantages, respectively. However, these structures do not effectively deal with a most serious problem: body fluid exuding from the surface of a wound, namely, exudate.

Heretofore, there have been common or accepted theories, such as a theory that how to discharge or absorb the exudate is important, from a viewpoint that the excess accumulation of the exudate capable of causing infection, etc., is seriously considered; or a theory that appropriate secretion and accumulation of the exudate are required in order to heal a wound, from a viewpoint that the excess dryness of the surface of the wound retards the healing thereof.

The above-mentioned type (1) of the wound-covering medium having a structure containing pores communicating with each other is based on the former theory that the efficient discharge of the exudate is seriously considered. Further, the above-mentioned type (3) of the wound-covering medium comprising fine particulate hydrogel is based on the theory that the exudate should be absorbed.

On the other hand, the above-mentioned type (2) of the wound-covering medium having a film structure having a poor porosity is based on the latter theory that the excess dryness of the wound surface should be prevented and a wetted condition thereof should be maintained so as to promote the healing of the wound.

However, in a case where the above-mentioned wound-covering medium having a good porosity is used, the discharge of the exudate is good, but the exudate or regenerated tissue penetrates into the pores of the covering medium, and it becomes very difficult to remove the covering medium from the wound at the time of the exchange of the covering medium or after the completion of the wound healing. In such a case, if the covering medium is forcedly removed from the wound, not only a portion of the tissue which has been already healed is damaged so as to seriously retard the healing of the wound, but also it is troublesome to remove the covering medium and such removal simultaneously causes severe patient discomfort. In addition, with respect to such a type of wound-covering medium, there have been pointed out some problems that it has an excess transpirability to moisture and therefore the wound surface is excessively dried so as to retard the healing of the wound; or the sizes of the communicating pores in the inside of the porous material are large, and therefore external bacteria undesirably reach the wound surface.

On the other hand, when the covering medium of the above type (2) having a poor porosity is used, although various problems with the above-mentioned porous covering medium have been solved, there is posed a new problem that a large amount of the exudate is accumulated between the covering medium and the wound surface, and such accumulation of the exudate is liable to be a hotbed of rapid growth of bacteria. Especially, the covering medium having a poor porosity is harder than the above-mentioned covering medium (1) having a good porosity, and therefore it is difficult to closely attach such a type of covering medium to the surface of a wound having a complex profile or shape. Further, when this type of the covering medium having a poor porosity is used, it has been pointed out the occurrence of a serious problem that a larger amount of the exudate is liable to be secreted.

In addition, when the covering medium of the type (3) which comprises a particulate hydrogel capable of actively absorbing the secreted exudate is used, the secretion of the exudate is further promoted as the covering medium absorbs a larger amount of the exudate. As a result, there has been posed a problem that the absorbing ability of the covering medium is saturated, the accumulation of the exudate at the wound surface is noticeably recognized as compared with that of the type (3) porous covering medium, and such accumulation of the exudate is liable to be a hotbed of rapid growth of bacteria.

As described above, the problems common to the conventional wound-covering media, i.e., the problems concerning the discharge and absorption of the exudate have still been left unsolved. An object of the present invention is to provide a wound-covering material which solves the above-mentioned problems encountered in the conventional wound-covering medium.

Another object of the present invention is to provide a wound-covering material which solves the problems of the discharge or absorption of exudate.

A further object of the present invention is to provide a wound-covering material which is capable of providing a wound-covering matter (or article) which may be positioned stably or left for a long period of time under a condition such that it is closely attached to the surface of a wound.

A further object of the present invention is to provide a wound-covering material which is capable of preventing the exudation, and is capable of healing the wound without the necessity of the exchange thereof.

A further object of the present invention is to provide a wound-covering material which is capable of providing a wound-covering article which may stably be positioned for a long time under a condition such that it is closely attached to the surface of a wound.

A further object of the present invention is to provide a wound-covering material which is capable of healing a wound without the necessity of implantation of skin, even in the case of a wide-range full-thickness skin wound.

A further object of the present invention is to provide a wound-covering material which is capable of effectively preventing the infection of a wound.

A further object of the present invention is to provide a wound-covering material which is capable of promoting the healing of a wound.

A further object of the present invention is to provide a wound-covering material having an analgesic function.

A still further object of the present invention is to provide a wound-covering composition which includes the above-mentioned wound-covering material and is capable of forming a desirable wound-covering matter on the surface of a wound.

DISCLOSURE OF INVENTION

As a result of earnest study, the present inventor has found that the "in-situ" formation of a wound-covering matter (e.g., in a film-like form) on the surface of a wound, which includes a material comprising a polymer having a sol-gel transition temperature in an aqueous solution thereof, and shows a substantial water-insolubility at a temperature higher than the above-mentioned transition temperature, and further shows a reversible water-solubility at a temperature lower than the transition temperature, may rather promote the healing of a wound, not only by easily providing a wound-covering article which is closely attachable to the surface of the wound having a complex profile, but also by effectively preventing the exudation on the basis of the thus formed wound-covering article.

As a result of further study, the present inventor has also found that the wound-covering matter formed in such a manner may satisfy both the adhesion property thereof to the wound surface, and easy removal of the wound covering matter from the wound of which healing has considerably been advanced.

The wound-covering material according to the present invention is based on the above discovery, and more specifically, it comprises: a polymer having a sol-gel transition temperature in an aqueous solution thereof, shows a substantial water-insolubility at a temperature higher than the sol-gel transition temperature, and shows a reversible water-solubility at a temperature lower than the sol-gel transition temperature.

The present invention also provides a wound-covering composition, which comprises, at least, water and a polymer having a sol-gel transition temperature in an aqueous solution thereof, assumes a liquid state (sol state) at a temperature lower than the sol-gel transition temperature, and assumes a gel state which is substantially water-insoluble at a temperature higher than the sol-gel transition temperature.

The present invention further provides a wound-covering medium, comprising a layer of a composition to be positioned or placed on the side of a wound, and a membrane having a low water vapor permeability disposed on the outside of the composition layer; the composition layer comprising, at least, water and a polymer which has a sol-gel transition temperature in an aqueous solution thereof, assumes a liquid state (sol state) at a temperature lower than the sol-gel transition temperature, and assumes a gel state which is substantially water-insoluble at a temperature higher than the sol-gel transition temperature.

According to the experiments conducted by the present inventor, the following findings have been obtained on the mechanism of the exudation from a wound.

More specifically, according to the experiments conducted by the present inventor, there has been found a phenomenon that the exudate is not secreted in normal tissue, but when a space is artificially provided in the normal tissue, the space is filled with body fluid secreted from the tissue surrounding the space, thereby to form a cyst-like structure. Therefore, according to the present inventor's findings, it is presumed that the secretion of the exudate is caused by a space provided between the wound surface and the covering medium on the basis of the above-mentioned phenomenon.

In the conventional wound-covering materials to which a predetermined profile or shape is initially imparted, it is considered that such a wound-covering material cannot be closely attached completely to the wound surface having a complex profile, but a certain space is provided between the covering material and the wound surface. Based on the presence of such a space, the exudate is secreted by the mechanism as described above, and is accumulated within the space.

In the contrast, the wound-covering material according to the present invention may be placed on the surface of a wound having a complex profile in a liquid state (sol state) on the basis of the characteristic of a polymer constituting the covering material (i.e., a polymer having a sol-gel transition temperature in an aqueous solution thereof), and may be rapidly converted into a semi-solid state (gel state). Accordingly, when the covering material according to the present invention is used, it is presumed that the material in a liquid state may be closely attached even to the surface of a wound having a complex profile, and substantially no space is provided between the material and the wound surface, and therefore there is substantially no exudation, whereby the accumulation of the exudate does not occur.

In the present invention, a hydrophilic portion of the above polymer imparts the polymer with a function of being converted into a water-soluble state at a temperature lower than the sol-gel transition temperature (e.g., a temperature lower than the temperature of the wound surface). On the other hand, a hydrophobic portion of the polymer imparts the polymer with a function of being converted into a gel state at a temperature higher than the sol-gel transition temperature (e.g., the temperature of the wound surface) In other words, the bonds between the above hydrophobic portions contribute to the formation of crosslinking points of the above gel.

The wound-covering material according to the present invention utilizes bonds between the hydrophobic portions in the above polymer, i.e., the property of the above hydrophobic bond as described hereinbelow.

The hydrophobic bond has a property such that the bonding strength thereof is increased along with an increase in temperature, and the crosslinking strength and crosslinking density thereof are increased along with an increase in temperature. Therefore, the wound-covering material according to the present invention assumes a liquid state at a temperature lower than the sol-gel transition temperature, and may be placed on the surface of a wound such that it is closely attached to the wound surface completely. In addition, crosslinkage due to the hydrophobic bond in the covering material is formed at a temperature (e.g., at the temperature of the wound surface) higher than the sol-gel transition temperature so that it assumes a gel state. As a result, the covering material according to the present invention may stably perform a function as a wound-covering material on the wound surface.

Further, since the temperature dependence of the above hydrophobic bond strength has a reversible property, the sol-gel transition occurs reversibly when the wound-covering material according to the present invention is used. Accordingly, in a case where such a property is utilized, when the wound-covering material according to the present invention becomes unnecessary (e.g., at the time of the completion of the wound healing), or when the covering material is to be exchanged, the covering material may easily be removed from the wound surface by lowering the temperature to a certain value lower than the sol-gel transition temperature (e.g., by lowering the temperature to a value lower than the wound temperature) so as to convert the material into a liquid state (sol state).

As described above, when the wound-covering material according to the present invention is used, the covering material may easily be removed from the wound surface simply by utilizing a temperature change alone, and therefore it is very easy to wash the wound surface or to exchange an effective antibiotic substance, at the time of the infection of the wound.

The polymer constituting the wound-covering material according to the present invention may preferably have a sol-gel transition temperature which is higher than 0° C. and not higher than 40° C. Since the temperature of the wound surface is generally 30°–40° C., the wound-covering material may preferably have, the wound-covering material may preferably have, at least, a sol-gel transition temperature of not higher than 40° C., in view of the maintenance of a stable gel state on the wound surface.

On the other hand, the hydrophilic portion in the above polymer imparts the polymer with a property of being converted into a water-soluble state at a temperature lower than the sol-gel transition temperature so that the hydrophilic portion imparts the material with a function of being easily removed from the wound surface at the time at which the wound-covering material is to be exchanged or the healing of the wound is completed. Simultaneously, the hydrophilic portion imparts the material with a function such that the material is capable of forming a water-containing gel while preventing the above polymer from being agglomerated or precipitated at a temperature not lower than the sol-gel transition temperature due to an excess increase in the hydrophobic bonding strength at a temperature higher than the above sol-gel transition temperature.

As specific examples of a polymer having a sol-gel transition temperature in an aqueous solution thereof and reversibly assuming a sol state at a temperature lower than the sol-gel transition temperature, there have been known, e.g., polyalkylene-oxide block copolymer represented by block copolymers comprising polypropylene oxide portions and polyethylene oxide portions; etherified (or ether group-containing) celluloses such as methyl cellulose and hydroxypropyl cellulose; chitosan derivatives, etc., (K. R. Holme. et al. Macromolecules, 24, 3828 (1991)).

In addition, there has been developed a wound-covering gel (R. M. Nalbandian et al., J. Biomed. Mater. Res., 6, 583 (1972); J. Biomed. Mater. Res., 12, 1135 (1987)) utilizing Pluronic F-127 (trade name, mfd. by BASF Wyandotte Chemical Co.) comprising a polypropylene oxide portion and polyethylene oxide portions bonded to the both terminals thereof.

It is known that a high-concentration aqueous solution of the above Pluronic F-127 is converted into a hydrogel at a temperature of not lower than about 20° C., is converted into an aqueous solution at a temperature lower than the above-mentioned temperature. However, this material can assume a gel state only at a high concentration of not lower than about 20 wt. %. In addition, even when such a gel having a high concentration of not lower than about 20 wt. % is maintained at a temperature of not lower than the gel-forming temperature, the gel is dissolved by further adding water thereto. Accordingly, when a gel comprising the above Pluronic F-127 is simply applied onto the surface of a wound, the gel is dissolved by the exudate from the wound surface, etc., and therefore it is difficult to maintain a stable gel state on the wound surface, and it is impossible to prevent the secretion of the exudate from the wound surface. In addition, since the molecular weight of the Pluronic F-127 is relatively low, and it shows an extremely high osmotic pressure at a high concentration of not less than about 20 wt. %, and simultaneously the Pluronic F-127 may easily permeate the cell membranes, whereby the Pluronic F-127 can adversely affect the wound surface.

On the other hand, in the case of an etherified cellulose represented by methyl cellulose, hydroxypropyl cellulose, etc., the sol-gel transition temperature thereof is as high as about 45° C. or higher (N. Sarkar, J. Appl. Polym. Science, 24, 1073, (1979)). Accordingly, when such an etherified cellulose is simply applied onto a wound surface, since the temperature of the wound surface is, at most, 37° C. or below, the material assumes a sol state and is dissolved by the exudate from the wound surface, etc., whereby the material cannot prevent the secretion of the exudate from the wound surface.

Further, the above-mentioned chitosan derivatives have a sol-gel transition temperature as high as about 50° C. (K. R. Holme. et al., Macromolecules, 24, 3828 (1991)). Accordingly, when such a chitosan derivative is simply applied to a wound surface, since the temperature of the wound surface is, at most, 37° C. or below, the material assumes a sol state and is dissolved by the exudate from the wound surface, etc., whereby the material cannot prevent the secretion of the exudate from the wound surface.

As described above, when a conventional polymer having a sol-gel transition temperature in an aqueous solution thereof, which reversibly assumes a sol state at a temperature lower than the above transition temperature, is simply applied to a wound surface, the following problems are posed:

(1) If the polymer is once converted into a gel state at the sol-gel transition temperature or above, the resultant gel is dissolved when water is further added thereto. That is, even if the polymer is converted into a gel state on a wound surface, the gel is dissolved by the exudate secreted from the wound surface, and the polymer cannot maintain a stable gel state for a long period of time. As a result, the polymer cannot prevent the secretion of the exudate from the wound surface.

(2) The polymer has a sol-gel transition temperature higher than the temperature of the wound surface (in the neighborhood of 37° C.), and therefore the polymer is not converted into a gel state on the wound surface, whereby the polymer cannot prevent the secretion of the exudate from the wound surface.

(3) It is necessary to increase the concentration of the polymer in an aqueous solution thereof to an extremely high value, in order to convert the polymer into a gel state.

According to the present inventor's investigation, it has been found that the above-mentioned problems have been solved by using a polymer having a sol-gel transition temperature in an aqueous solution thereof so as to constitute a wound-covering material which substantially shows a water-insolubility at a temperature higher than the sol-gel transition temperature, and reversibly shows a water-solubility at a temperature lower than the sol-gel transition temperature.

BEST MODE FOR CARRYING OUT THE INVENTION

Figure 1:
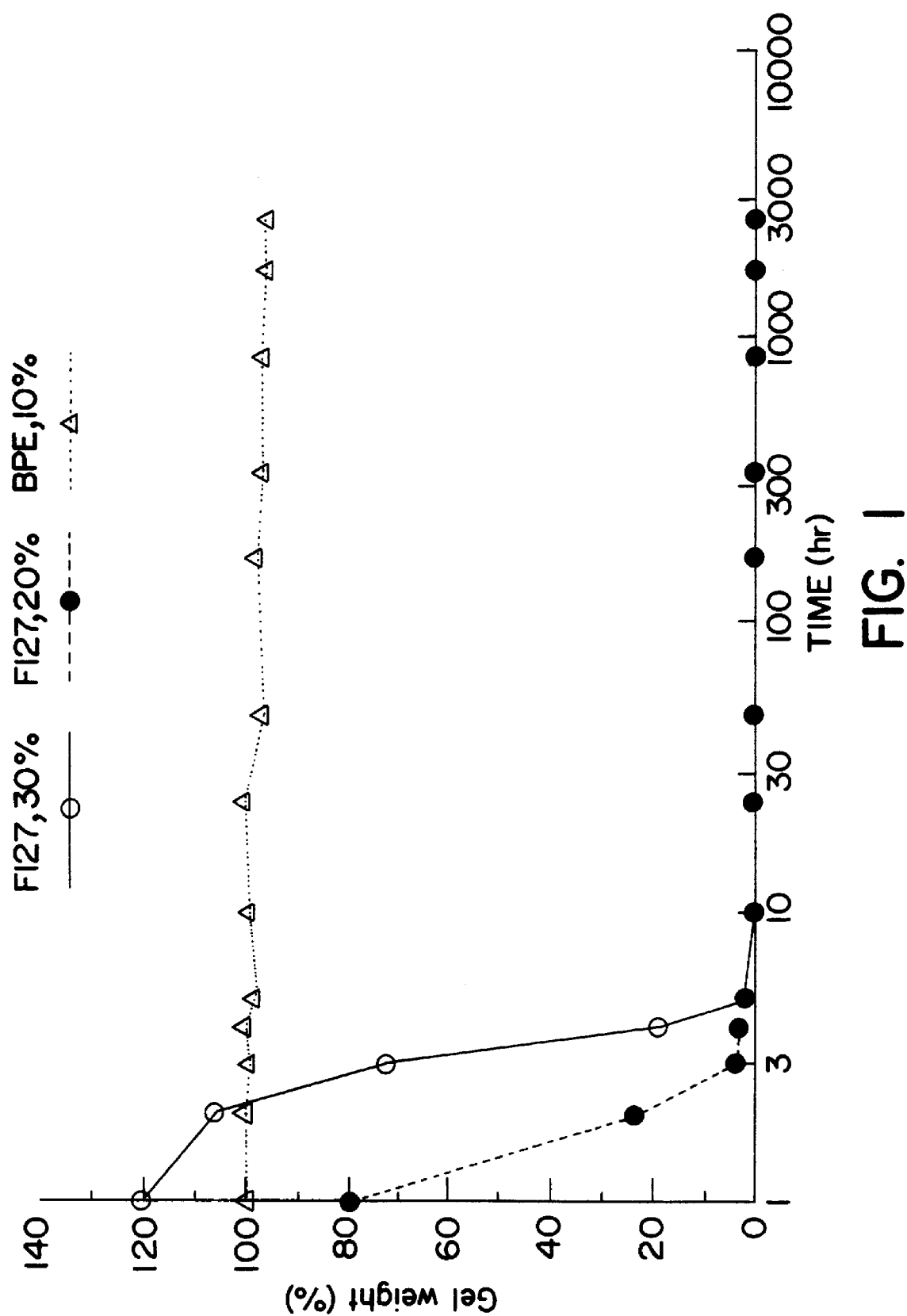
FIG. 1 is a graph showing the results of the measurement of a weight change in water, which have been obtained in Example 3 appearing hereinbelow with respect to a BPE (a polymer obtained in Example 1 appearing hereinbelow) gel, and Pluronic F-127 gels (having concentrations of 20% and 30%).

Hereinbelow, the present invention will be described in detail with reference to the accompanying drawings as desired. In the description appearing hereinafter, "%" and "part(s)" for describing quantities or ratios thereof are by weight unless otherwise noted specifically.

Sol-gel transition temperature

In the present invention, the terms "sol state" "gel state" and "sol-gel transition temperature" are defined in the following manner. With respect to these definitions, a paper (Polymer Journal, 18(5), 411–416 (1986)) may be referred to.

1 ml of a solution of a polymer is poured into a test tube having an inside diameter of 1 cm, and is left standing for 12 hours in a water bath which is controlled at a predetermined (constant) temperature. Thereafter, in a case where the interface (meniscus) between the solution and air is deformed (inclusive a case wherein the solution flows out from the test tube) due to the weight of the solution per se when the test tube is turned upside down, the above polymer solution is defined as a "sol state" at the above-mentioned predetermined temperature.

On the other hand, in a case where the interface (meniscus) between the solution and air is not deformed due to the weight of the solution per se even when the test tube is turned upside down, the above polymer solution is defined as a "gel state" at the above-mentioned predetermined temperature.

In addition, in a case where a polymer solution having a concentration of, e.g., about 3 wt. % is used in the above-mentioned measurement, and the temperature at which the "sol state" is converted into the "gel state" is determined while gradually increasing the above "predetermined temperature" (e.g., in 1° C. increment), the thus determined transition temperature is defined as a "sol-gel transition temperature". At this time, alternatively, it is also possible to determine the above temperature at which the "gel state" is converted into the "sol state" while gradually decreasing the "predetermined temperature" (e.g., in 1° C. decrement)

In the present invention, the above sol-gel transition temperature may preferably be higher than 0° C. and not higher than 40° C. (more preferably, not lower than 4° C. and not higher than 37° C.) in view of the balance between the stability of the wound-covering material placed on a wound surface, and the ease of removal of the covering material from the wound surface. The polymer having such a preferred sol-gel transition temperature may be easily selected from specific compounds as described below, according to the above-mentioned screening method (method of measuring the sol-gel transition temperature).

In the wound-covering material according to the present invention, it is preferred to set the above-mentioned sol-gel transition temperature (a °C.) between the temperature at which a wound-covering article based on such a material is to be formed on a wound surface (b °C.; e.g., the temperature of an aqueous solution), and the temperature on the wound surface (c °C.). In other words, the above-mentioned three kinds of temperatures of a °C., b °C. and c °C. may preferably have a relationship of b<a<c. More specifically, the value of (a–b) may preferably be 1°–35° C., more preferably 2°–30° C. On the other hand, the value of (c–a) may preferably be 1°–35° C., more preferably 2°–30° C.

Plural blocks having cloud point

The plural blocks having a cloud point may preferably comprise a polymer which shows a negative solubility-temperature coefficient with respect to water. More specifically, such a polymer may preferably be one selected from the group of:
polypropylene oxide, copolymers comprising propylene oxide and another alkylene oxide, poly N-substituted acrylamide derivatives, poly N-substituted methacrylamide derivatives, copolymers comprising an N-substituted acrylamide derivative and an N-substituted methacrylamide derivative, polyvinyl methyl ether, and partially-acetylated product of polyvinyl alcohol. It is preferred that the above polymer (block having a cloud point) has a cloud point of higher than 020 C. and not higher than 40° C., in view of the provision of a polymer (compound comprising a plurality of blocks having a cloud point, and a hydrophilic block bonded thereto) to be preferably used in the present invention having a sol-gel transition temperature of higher than 0° C. and not higher than 40° C.

It is possible to measure the cloud point, e.g., by the following method. That is, an about 1 wt. %-aqueous solution of the above polymer (block having a cloud point) is cooled to be converted into a transparent homogeneous solution, and thereafter the temperature of the solution is gradually increased (temperature increasing rate: about 1° C./min.), and the point at which the solution first shows a cloudy appearance is defined as the cloud point.

Specific examples of the poly N-substituted acrylamide derivatives and poly N-substituted methacrylamide derivatives are described below.

Poly-N-acryloyl piperidine
Poly-N-n-propyl methacrylamide
Poly-N-isopropyl acrylamide
Poly-N-diethyl acrylamide
Poly-N-isopropyl methacrylamide
Poly-N-cyclopropyl acrylamide
Poly-N-acryloyl pyrrolidine
Poly-N,N-ethyl methyl acrylamide
Poly-N-cyclopropyl methacrylamide
Poly-N-ethyl acrylamide The above polymer may be either a homopolymer or a copolymer comprising a monomer constituting the above polymer and "another monomer". The "another monomer" to be used for such a purpose may be a hydrophilic monomer, or a hydrophobic monomer. In general, when copolymerization with a hydrophilic monomer is conducted, the resultant cloud point may be increased. On the other hand, when copolymerization with a hydrophobic monomer is conducted, the resultant cloud point may be decreased. Accordingly, a polymer having a desired cloud point (e.g., a cloud point of higher than 0° C. and not higher than 40° C.) may be obtained by selecting such a monomer to be used for copolymerization.

Specific examples of the above hydrophilic monomer may include: N-vinyl pyrrolidone, vinyl pyridine, acrylamide, methacrylamide, N-methyl acrylamide, hydroxyethyl methacrylate, hydroxyethyl acrylate, hydroxymethyl methacrylate, hydroxymethyl acrylate, methacrylic acid and acrylic acid having an acidic group, and salts of these acids, vinyl sulfonic acid, styrenesulfonic acid, etc., and derivatives having a basic group such as N,N-dimethylaminoethyl methacrylate, N,N-diethylaminoethyl methacrylate, N,N-dimethylaminopropyl acrylamide, salts of these derivatives, etc. However, the hydrophilic monomer to be usable in the present invention is not restricted to these specific examples.

On the other hand, specific examples of the above hydrophobic monomer may include: acrylate derivatives and methacrylate derivatives such as ethyl acrylate, methyl methacrylate, and glycidyl methacrylate; N-substituted alkyl methacrylamide derivatives such as N-n-butyl methacrylamide; vinyl chloride, acrylonitrile, styrene, vinyl acetate, etc. However, the hydrophobic monomer to be usable in the present invention is not restricted to these specific examples.

Hydrophilic block

On the other hand, specific examples of the hydrophilic block to be combined with (or bonded to) the above-mentioned block having a cloud point may include: methyl cellulose, dextran, polyethylene oxide, polyvinyl alcohol, poly N-vinyl pyrrolidone, polyvinyl pyridine, polyacrylamide, polymethacrylamide, poly N-methyl acrylamide, polyhydroxymethyl acrylate, polyacrylic acid, polymethacrylic acid, polyvinyl sulfonic acid, polystyrene sulfonic acid, and salts of these acids; poly N,N-dimethylaminoethyl methacrylate, poly N,N-diethylaminoethyl methacrylate, poly N,N-dimethylaminopropyl acrylamide, and salts of these, etc.

The process for combining the above block having a cloud point with the hydrophilic block is not particularly limited. For example, it is possible to conduct such a combination by introducing a polymerizable functional group (such as acryloyl group) into either one of the above blocks, and copolymerizing with the resultant product a monomer capable of providing the other block.

Alternatively, it is also possible to obtain a combination product of the above block having a cloud point with the hydrophilic block by copolymerizing a monomer capable of providing the block having a cloud point with a monomer capable of providing the hydrophilic block.

In addition, the block having a cloud point and the hydrophilic block may also be combined or bonded with each other by preliminarily introducing reactive functional groups (such as hydroxyl group, amino group, carboxyl group, and isocyanate group) into both kinds of the blocks, and combining these blocks by using a chemical reaction. At this time, it is usual to introduce a plurality of reactive functional groups into the hydrophilic block.

Further, the polypropylene oxide having a cloud point and the hydrophilic block may be combined or bonded with each other by repetitively subjecting polypropylene oxide and a monomer constituting the above "other water-soluble polymer" (such as ethylene oxide) to a stepwise or consecutive polymerization, thereby to obtain a block copolymer comprising polypropylene oxide and the "other water-soluble polymer" (such as polyethylene oxide) combined therewith.

Such a block copolymer may also be obtained by introducing a polymerizable group (such as acryloyl group) into the terminal of polypropylene oxide, and then copolymerizing therewith a monomer constituting the water-soluble polymer.

Further, a polymer usable in the present invention may be obtained by introducing a functional group which is reactive in a bond-forming reaction with the terminal functional group of polypropylene oxide (such as hydroxyl group) into a water-soluble polymer, and reacting the resultant water-soluble polymer and the polypropylene oxide. In addition, a polymer usable in the present invention may be obtained by connecting materials such as one comprising polypropylene glycol and polyethylene glycol bonded to both terminals thereof (such as Pluronic F-127; trade name, mfd. by Asahi Denka Kogyo K.K.).

At a temperature lower than the cloud point, the polymer preferably usable in the present invention (a compound comprising a plurality of blocks having a cloud point, and a hydrophilic block combined therewith) may be completely dissolved in water so as to assume a sol state, since the above-mentioned "block having a cloud point" present in the polymer molecule is water-soluble together with the hydrophilic block.

However, when a solution of the above polymer is heated up to a temperature not lower than the cloud point, the "block having a cloud point" present in the polymer molecule becomes hydrophobic so that separate molecules of the polymer are associated or aggregated with each other due to a hydrophobic interaction.

On the other hand, the hydrophilic block is water-soluble even at this time (i.e., even when heated up to a temperature not lower than the cloud point), and therefore, the polymer according to the present invention in water is formed into a hydrogel having a three-dimensional network structure wherein hydrophobic association portions between the blocks having a cloud point constitute crosslinking points. The temperature of the resultant hydrogel is again cooled to a temperature lower than the cloud point of the "block having a cloud point" present in the polymer molecule, the block having a cloud point becomes water-soluble and the above crosslinking points due to the hydrophobic association are released or liberated so that the hydrogel structure disappears, whereby the polymer according to the present invention is again formed into a complete aqueous solution. In the above-described manner, the sol-gel transition in the polymer according to the present invention is based on the reversible hydrophilic-hydrophobic conversion in the block having a cloud point present in the polymer molecule at the cloud point, and therefore the transition has a complete reversibility in accordance with a temperature change.

Wound-covering material

As described above, the wound-covering material according to the present invention comprising at least a polymer having a sol-gel transition temperature in an aqueous solution thereof, substantially shows a water insolubility at a temperature (d °C.) higher than the sol-gel transition temperature, and reversibly shows water solubility at a temperature (e °C.) lower than the sol-gel transition temperature.

The above-mentioned temperature (d °C.) may preferably be a temperature which is at least 1° C., more preferably at least 2° C. (particularly preferably, at least 5° C.) higher than the sol-gel transition temperature. Further, the above-mentioned "substantial water insolubility" may preferably be a state wherein the amount of the above polymer to be dissolved in 100 ml of water at the above temperature (d °C.) is 5.0 g or less (more preferably 0.5 g or less, particularly preferably 0.1 g or less).

On the other hand, the above-mentioned temperature (e °C.) may preferably be a temperature which is at least 1° C., more preferably at least 2° C. (particularly preferably, at least 5° C.) lower than the sol-gel transition temperature. Further, the above-mentioned "water solubility" may preferably be a state wherein the amount of the above polymer to be dissolved in 100 ml of water at the above temperature (e °C.) is 0.5 g or more (more preferably 1.0 g or more). The above "to show a reversible water solubility" refers to a state wherein an aqueous solution of the above wound-covering material shows the above-mentioned water solubility at a temperature lower than the sol-gel transition temperature, even when it is once formed into a gel state (at a temperature higher than the sol-gel transition temperature).

A 10%-aqueous solution of the above polymer may preferably show a viscosity of 10–3,000 centipoises, (more preferably, 50–1,000 centipoises) at 5° C. Such a viscosity may preferably be measured, e.g., under the following measurement conditions:

Viscometer: Stress-controlled type rheometer (model: CSL-500, mfd. by Carri-Med Co., USA)

Rotor diameter: 60 mm

Rotor configuration: Parallel-plate type

Measurement frequency: 1 Hz (hertz)

Even when the an aqueous solution of the wound-covering material according to the present invention is formed into a gel state at a temperature higher than the sol-gel transition temperature, and thereafter the resultant gel is immersed in a large amount of water, the gel is not substantially dissolved in water. For example, such a characteristic of the above covering material may be confirmed in the following manner.

More specifically, 0.15 g of the wound-covering material according to the present invention is dissolved in 1.35 g of distilled water at a temperature lower than the above sol-gel transition temperature (e.g., under cooling with ice) thereby to prepare a 10 w %-aqueous solution. Then, the resultant solution is poured into a plastic Petri dish having a diameter of 35 mm, then the dish is warmed up to a temperature of 37° C. to form a gel having a thickness of about 1.5 mm in the dish, and the total weight of the Petri dish (f gram) containing the gel is measured. Then, the entirety of the Petri dish containing the gel is left standing in 250 ml of water at 37° C. for 10 hours, and thereafter the total weight of the Petri dish (g gram) containing the gel is measured, thereby to determine whether the gel has been dissolved from the gel surface or not. At this time, in the wound-covering material according to the present invention, the ratio of weight decrease in the gel, i.e., the value of {(f−g)/f} may preferably be 5.0% or less, more preferably 1.0% or less (particularly preferably 0.1 % or less).

Even when an aqueous solution of the wound-covering material according to the present invention was converted into a gel state at a temperature higher than the sol-gel transition temperature, and then the resultant gel was immersed in a large amount (about 0.1–100 times larger than the gel, by volume ratio), the gel was not dissolved for a long period of time (as shown by Example 3 appearing hereinafter). In contrast, in a case where a similar gel was formed by using the above-mentioned Pluronic F-127 comprising polypropylene oxide and polyethylene oxide bonded to both terminals thereof, the resultant gel was completely dissolved when the gel is left standing in water for several hours.

The above-mentioned property of the wound-covering material according to the present invention is important in view of the long-term prevention of the exudation on a wound surface. Such a property has never been found in the conventional wound-covering materials. The properties of the wound-covering material according to the present invention may be provided, e.g., by using a polymer having a plurality of blocks having a cloud point in one molecule as described above.

According to the present inventor's findings, in the case of the above-mentioned Pluronic F-127, it is presumed that one molecule thereof has only one block having a cloud point (i.e., polypropylene oxide block) present therein, and the crosslinking structure between hydrophobic groups to be formed at temperature higher than the sol-gel transition temperature is weak or fragile, and therefore the gel based on the Pluronic F-127 is dissolved in water. On the other hand, in the case of the wound-covering material according to the present invention, it is presumed that a gel having a firm crosslinking structure is formed since the polymer used therein has two or more hydrophobic blocks in one molecule, and the water-resistance of the resultant gel is improved.

The wound-covering material according to the present invention comprises at least the above-mentioned polymer having a sol-gel transition temperature, but may further comprise another component as desired. Specific examples of the "other component" in such an embodiment may include: e.g., an analgesic agent, etc., in addition to an antibacterial agent and a wound healing-accelerator as described below. In such a case, it is preferred to use the "other component" in an amount of 0.5–30 parts, more preferably 1–10 parts, with respect to 100 (weight) parts of the polymer having a sol-gel transition temperature.

Antibacterial agent

In the present invention, an antibacterial agent for external use which has widely been used for clinical purposes at present, may preferably be used for the above antibacterial agent. More specifically, preferred examples thereof may include: e.g., silver nitrate, para-aminobenzene sulfamide, gentamicin, silver sulfadiazine, nalidixic acid, piromidic acid pipemidic acid, norfloxacin, ofloxacin, cyprofloxacin, etc. However, the antibacterial agents to be usable are not limited to these specific examples.

It is preferred to use the above antibacterial agent in an amount of 0.5–30 parts, more preferably 1–10 parts, with respect to 100 parts of the polymer according to the present invention.

Wound healing-accelerators

In the present invention, it is preferred to use a cytokine and/or an extracellular matrix having an effect of increasing the affinity with tissue and simultaneously promoting epithelization, as the above wound healing-accelerator. More specifically, preferred examples thereof may include: e.g., extracellular matrixes such as various types of collagens, fibronectin, vitronectin, laminin, proteoglycon, and glycosaminoglycan; cytokines such as TGF (tumor growth factor), FGF(fibloblast growth factor), and PDGF (platelet-derived growth factor). In addition to the extracellular matrix or cytokine, thermally denatured products of collagen such as gelatine have a similar effect, and therefore these substances may also be used similarly as the above-mentioned extracellular matrix, etc.

It is preferred to use the above extracellular matrix in an amount of 0.1–50 parts, more preferably 1–20 parts, with respect to 100 parts of the polymer according to the present invention.

On the other hand, it is preferred to use the above cytokine in an amount of about 0.1–100 ng with respect to 1 g of the polymer according to the present invention.

In a case where the above-mentioned antibacterial agent, wound healing-accelerator, etc., is incorporated into the wound-covering material according to the present invention, for example, it is possible to adopt a method wherein the antibacterial agent, wound healing-accelerator, etc., are dissolved or dispersed in an aqueous solution of the above covering material at a temperature lower than the sol-gel transition temperature of the covering material.

Wound-covering composition

The wound-covering composition according to the present invention is a composition which comprises, at least, water and the polymer as described hereinabove; which a liquid state (sol state) at a temperature lower than the sol-gel transition temperature; and which a gel state which is substantially insoluble in water at a temperature higher than the sol-gel transition temperature.

In the wound-covering composition according to the present invention, it is preferred to use water in an amount of about 40–2000 parts (more preferably about 90–500 parts) with respect to 10 parts of the above polymer.

In this case, the meanings of the above-mentioned "temperature (e °C.) lower than the sol-gel transition temperature" and "temperature (d °C.) higher than the sol-gel transition temperature" are the same as those described with respect to the wound-covering material according to the present invention. In addition, the meaning of "substantially insoluble in water" is the same as that described with respect to the gel based on the wound-covering material according to the present invention.

The above composition (in a state such that it is present immediately before the application thereof to a wound) may preferably show a viscosity of 10–3,000 centipoises (more preferably 50–1,000 centipoises) at 5° C. Such a viscosity may be measured, e.g., under viscosity measurement conditions which are the same as those described with respect to the wound-covering material according to the present invention.

In the wound-covering composition according to the present invention, it is also possible to use an aqueous medium such as physiological saline (physiological salt solution), Ringer's solution, buffer, and culture medium, instead of the above-mentioned water.

The wound-covering composition according to the present invention may also contain, in addition to the above polymer and water, a liquid substance other than water. Specific examples usable of such a substance may include: e.g., water-soluble liquids including alcohols (e.g., monohydric, dihydric and trihydric alcohols) such as ethanol, ethylene glycol, propylene glycol, and glycerin;

oily liquids such as vegetable oil, liquid paraffin, and animal oil (an oily liquid is used after it is converted into a suspension or emulsion as desired). In a case where such a liquid substance is used, it is preferred to use the liquid in an amount of about 0.1–100 parts, more preferably about 1–50 parts with respect to 100 parts of water.

The wound-covering composition according to the present invention comprises at least water and the above-mentioned polymer having a sol-gel transition temperature, but may further comprise another component as desired. Specific examples of the "other component" in such an embodiment may include: e.g., an antibacterial agent, a wound healing-accelerator, an analgesic agent, etc., as described above. In such a case, it is preferred to use the "other component" in an amount of 0.5–30 parts, more preferably 1–10 parts, with respect to 100 parts of the polymer having a sol-gel transition temperature.

Method of using wound-covering material

Hereinbelow, there is specifically described a preferred method of actually using the wound-covering material according to the present invention.

For example, at a temperature lower than the sol-gel transition temperature of the polymer constituting the wound-covering material according to the present invention, the covering material is dissolved in an aqueous medium such as physiological salt solution, Ringer's solution, and culture medium so as to provide a concentration of 0.5%–20% (more preferably 2%–10%). At this time, it is also possible to add an antibacterial agent, a wound healing-accelerator, etc., to the aqueous solution of the above-mentioned wound-covering material, as desired, by a method as described hereinabove.

Then, the resultant aqueous solution of the wound-covering material (i.e., an embodiment of the wound-covering composition according to the present invention) is maintained at a temperature lower than the above sol-gel temperature, and is placed (or placed) on the surface of a wound while maintaining the aqueous solution state.

The method of placing or pouring the aqueous solution of the wound-covering material on the surface of a wound is not particularly limited, as long as it is possible to form a wound-covering matter in the form of a sheet or film (or membrane) as described hereinbelow on the wound surface. More specifically, it is possible to appropriately use, e.g., a method wherein the above-mentioned aqueous solution is dropped or dripped onto the wound surface by means of a dripping device such as syringe and pipet, a method wherein the solution is applied onto the wound surface by means of an application device such as brush, a method wherein the solution is applied onto the wound surface by spraying, etc.

When the temperature of the aqueous solution of the above covering material reaches the temperature of the surface of a wound (i.e., a temperature higher than the sol-gel transition temperature), the aqueous solution is converted into a gel state so that it may be stably fastened onto the wound surface (as a wound-covering article). In such a manner, the thickness of the wound-covering material which has been formed along the wound surface usually having a complex profile or outline, generally becomes non-uniform. Such a thickness (average thickness) is not particularly limited as long as the above covering matter may be stably placed onto wound surface. In view of the balance between the rate of gel formation and gel strength, in general, the thickness may preferably be 0.1–10 mm (more preferably 0.5–5 mm).

It is preferred to cover the upper surface of the wound-covering matter with a flexible film such as polyurethane, silicone elastomer, in order to prevent the excess transpiration or vaporization of water form the resultant gel, after the wound-covering matter in a gel form is formed in the above-described manner.

The above-mentioned film may preferably have a low water vapor permeability. The film may preferably have a water vapor permeability of about 800 $(g/m^2 \cdot 24\ hr)$ or below, more preferably about 500 $(g/m^2 \cdot 24\ hr)$ or below, particularly preferably about 300 $(g/m^2 \cdot 24\ hr)$ or below at 25° C., when converted into the value thereof in the case of a 25 $\mu$m-thick membrane. With respect to the details of the measurement method for such a water vapor permeability, e.g., a paper entitled "Makugaku Jikken-ho (Experimental procedures for Membranes)", edited by Masayuki Nakagaki, 209–227 pages (XV. Experimental procedures for gas permeability in synthetic polymer membranes), published by Kitami Shobo Co. (1984) may be referred to. The thickness of the film is not limited as long as it can prevent the excess transpiration or vaporization of water from the wound-covering matter in a gel state. In general, the thickness may preferably be about 1 $\mu$m–2 $\mu$m (2,000 $\mu$m), more preferably about 5 $\mu$m–0.5 mm (500 $\mu$m). The material constituting the film is not particularly limited as long as it is within a range corresponding to the above-mentioned "preferred water vapor permeability and thickness".

The wound-covering material according to the present invention can be colored as desired. The above-mentioned gel based on the covering material can be made translucent or opaque, but may preferably have a high transparency so that the degree of the healing of the wound surface may be observed from the outside of the gel. From such a viewpoint, it is preferred that the above-mentioned "flexible film" for covering the upper surface of the wound-covering matter according to the present invention is also excellent in transparency.

In a case where the above-mentioned wound-covering material is removed from the wound surface for a certain reason such as the completion of the healing of the wound, and the infection of the wound surface, the covering matter is cooled to a temperature lower than the above sol-gel transition temperature so as to convert the covering matter into a liquid state (sol state), whereby the covering matter may easily be removed from the wound surface.

It is preferred to use the wound-covering material or wound-covering composition according to the present invention for the purpose of covering a wound, after the covering material or composition is sterilized. The sterilization method used for such a purpose is not particularly limited, but it is preferred to use, e.g., autoclave sterilization.

In an embodiment wherein the above-mentioned wound-covering composition is used in combination with the above-mentioned membrane (film) having a low-water vapor permeability, there may be used a method wherein a layer (in a gel state) comprising the wound-covering composition is formed on the surface of a wound, and thereafter a low-water vapor permeability membrane is placed onto the outside of the composition layer (i.e., the side of the composition layer opposite to the wound surface side thereof) to thereby constitute a wound-covering medium in-situ; or a method wherein a composition layer having a predetermined thickness is placed on a low water vapor permeability membrane (or such a layer is formed on the membrane by coating), to thereby preliminarily prepare a wound-covering medium.

When the wound-covering medium of the latter type, i.e., a wound-covering medium comprising a film and a composition layer which has preliminarily been formed thereon is used, it is possible to cover a wound, e.g., by placing the wound-covering material onto the wound surface so that the composition layer side thereof contacts the wound surface, and thereafter cooling the wound-covering material by using appropriate cooling means (such as cooling spray, cold insulator or cold-reserving material, and ice bag) so as to once convert the composition layer into a sol state, and then removing the cooling means so as to convert the composition layer into a gel state on the basis of body temperature.

Hereinbelow, the present invention will be described in more detail with reference to examples. However, it should be noted that the present invention is defined by claims, but is not limited by the following examples.

EXAMPLE 1

160 mol of ethylene oxide was subjected to an addition reaction with 1 mol of trimethylol propane by cationic polymerization, thereby to obtain polyethylene oxide triol. 0.02 mol of the thus obtained polyethylene oxide triol was dissolved in 100 ml of distilled water, and then 0.1 mol of potassium permanganate was added thereto and the resultant mixture was subjected to an oxidization reaction at 25° C. for 60 minutes, to thereby obtain a polyethylene oxide tricarboxyl derivative.

10 g of the thus obtained polyethylene oxide tricarboxyl derivative, 5 g of polypropylene oxide diamino derivative (average propylene oxide polymerization degree: about 65, Jeffamine D-4000, mfd. by Jefferson Chemical Co., U.S.A.) and 5 g of both terminal-aminated polyethylene oxide (molecular weight=6000, mfd. by Kawaken Fine Chemical K.K.) were dissolved in 1000 ml of carbon tetrachloride, and then 1.2 g of dicyclohexyl carbodiimide was added thereto, and the resultant mixture was allowed to undergo reaction for 6 hours under refluxing at the boiling point of the mixture. The resultant reaction mixture was cooled and filtered, and thereafter the solvent therein was distilled off under reduced pressure. Then, the resultant residue was dried under vacuum, thereby to obtain a polymer (BPE) as a wound-covering material according to the present invention.

The above-mentioned polymer BPE was dissolved in distilled water under cooling with ice so as to provide a concentration of 8%. When the resultant aqueous solution was gradually warmed, it was found that the viscosity thereof was gradually increased from 5° C., and it was converted into a hydrogel at about 10° C. When the resultant hydrogel was cooled, it was converted into an aqueous solution state at 5° C. Such an aqueous solution (sol)—gel conversion could be observed reversibly and repetitively.

EXAMPLE 2

9.61 g of N-isopropyl acrylamide (mfd. by Kojin K.K.), 0.71 g of n-butyl methacrylate (mfd. by Wako Junyaku Kogyo K.K.), and 1.12 g of methacryloyl isocyanate (mfd. by Nippon Paint K.K.) were dissolved in 400 ml of chloroform contained in a reaction vessel. After the inside of the reaction vessel was purged with nitrogen gas, 0.135 g of N,N-azobisisobutyronitrile was added thereto, and the resultant mixture was subjected to polymerization at 60° C. for 6 hours. The reaction mixture was concentrated, and then was reprecipitated in diethyl ether to agglomerate precipitate particles. The resultant precipitate was dried under vacuum, thereby to obtain 7.8 g of poly (N-isopropyl acrylamide-co-methacryloyl isocyanate-co-n-butyl methacrylate).

Then, 1.0 g of the thus obtained poly (N-isopropyl acrylamide-co-methacryloyl isocyanate-co-n-butyl methacrylate) and 0.5 g of both terminal-aminated polyethylene oxide (molecular weight=6000, mfd. by Kawaken Fine Chemical K.K.) were dissolved in 100 ml of chloroform, and the resultant mixture was allowed to undergo reaction at 50° C. for 3 hours.

The reaction mixture was cooled to room temperature, and thereafter 0.1 g of isopropylamine was added thereto, and was left standing for 1 hour. The reaction mixture was concentrated, and then was precipitated in diethyl ether. The resultant precipitate was separated by filtration, and then dried under vacuum, to thereby obtain 1.5 g of a polymer (GYM) as a wound-covering material according to the present invention.

0.5 g of the thus obtained polymer (GYM) was dissolved in 10 ml of distilled water under cooling with ice. When the resultant aqueous solution was gradually warmed, it was found that the solution lost its fluidity at about 20° C. or above, so as to be converted into a gel state. When the resultant gel was cooled, it recovered its fluidity at about 20° C. or below, so as to be again converted into an aqueous solution. Such a sol-gel transition conversion was reversibly and repetitively observed. The above polymer had a sol-gel transition temperature of about 20° C.

EXAMPLE 3

An aqueous solution (a wound-covering composition according to the present invention) of the BPE obtained in Example 1 was converted into a gel state, and then immersed in a large amount of water at 37° C., whereby the dissolution characteristic of the resultant gel was measured with the elapse of time. Separately, as a comparative experiment, the above-mentioned Pluronic F-127 (hereinafter, simply referred to as "F-127") was similarly converted into a gel, and the dissolution characteristic of the resultant gel was measured in water at 37° C.

More specifically, the above-mentioned dissolution characteristic was evaluated in the following manner.

That is, 0.15 g of the polymer (BPE) synthesized in Example 1 was dissolved in 1.35 g of distilled water under cooling with ice, thereby to prepare an aqueous solution having a concentration of 10%. Thereafter, the resultant solution was poured into a plastic Petri dish having a diameter of 35 mm, then the dish was warmed up to a temperature of 37° C. to form a gel having a thickness of about 1.5 mm in the dish, and the total weight of the Petri dish (initial weight) containing the gel was measured.

Then, the entirety of the Petri dish containing the gel was left standing in 250 ml of water at 37° C. for a predetermined period of time, and thereafter the Petri dish was taken out of the water, and the total weight of the Petri dish containing the gel was measured with the elapse of time, thereby to determine the difference between the thus measured weight and the above-mentioned initial weight. In this manner, the dissolution behavior of the gel (from the gel surface being in contact with water) into water was evaluated.

As comparative experiments, each of 0.3 g and 0.45 g of the above F-127 was dissolved in 1.2 g or 1.05 g of distilled water, respectively, under cooling with ice, to thereby prepare an aqueous solution of the F-127 having a concentration of 20% and 30%, respectively. By using the thus obtained aqueous solutions, the dissolving behaviors of these aqueous solutions were evaluated in the same manner as in the case of the above BPE, by preparing a gel having a thickness of about 1.5 mm in a Petri dish, and leaving it standing in 250 ml of water at 37° C. The results obtained by these experiments are shown in the graph of FIG. 1.

It was considered that the above-mentioned dissolution experiments simulated the dissolution behavior of the gel toward exudate, when the gel was placed on the surface of a wound.

As shown in the above FIG. 1, in any of the cases of the Pluronic F-127 gels having concentrations of 20% and 30%, respectively, the gels were completely dissolved in water within several hours. On the contrary, in case of the gel of the wound-covering material (BPE) according to the present invention, it was found that the gel was not substantially dissolved for 10 weeks. These results of the experiments suggest that in the case of the Pluronic F-127, the resultant gel was very unstable on the wound surface, but in the case of the wound-covering material according to the present invention, the resultant gel could be placed on the wound surface very stably.

EXAMPLE 4

Several of Wistar rats (male) having a weight of 250–350 g were anesthetized by ether, and then a surface portion of each rat extending from the left dorsal region to the left lateral region of abdomen was shaved and disinfected. In such a portion, a full-thickness skin wound having a size of 2.0×2.0 cm or 4.0×4.0 cm was aseptically removed, and then the bleeding from the wound surface was completely controlled.

Then, the wound-covering material (BPE) prepared in Example 1 was dissolved in physiological saline under cooling with ice so as to provide a concentration of 10 w %, and thereafter the resultant mixture was sterilized by means of an autoclave (121° C., 20 min.), and then was again dissolved in physiological saline under cooling with ice. The resultant physiological saline solution of BPE cooled with ice was sucked in a cooled pipet and was poured into the above-mentioned full-thickness skin wound. The amount of the thus poured solution was about 1.2 ml in the case of the deficient wound of 2.0×2.0 cm, and about 2.5 ml in the case of the deficient wound of 4.0×4.0 cm.

After the above BPE solution, the conversion thereof into a gel state was promoted due to the temperature of the wound surface, and was completely converted into a gel state after about one min later, thereby to provide a wound-covering matter (thickness: about 3 mm when evaluated through naked eye observation) which comprised the BPE gel and was closely attached to the wound surface having a complex profile. About 2 to 3 min. after the BPE solution was poured, the outer surface of the gel was covered with a 1mm-thick transparent polyurethane film (a membrane having a low-water vapor permeability) for the purpose of protecting the wound surface covered with the BPE gel, and maintaining the wetted state of the BPE gel. Thereafter, the outer surface of the transparent polyurethane film was bandaged under pressure by means of an elastic band (Elastoband).

With the elapse of time, the gel state of the thus covered BPE gel was observed with the naked eye for the presence or absence of the accumulation of exudate from the wound surface. Further, the area of the wound surface was measured by taking photographs thereof at intervals of one week. In addition, pathological examinations were performed at 2, 3, 4, 5 and 10 weeks, respectively, counted from the gel formation.

In a case where the above BPE gel was used, in each of the deficient wound of 2.0×2.0 cm, and that of 4.0×4.0 cm, within the period of time during which the above observation was performed, no accumulation of exudate between the BPE gel and the wound surface was observed, the gel did not float above the wound surface and flow away, and was not dissolved and extinguished, but the BPE gel completely covered the wound surface in close contact. Moreover, the BPE gel increased its gel strength along with the decrease in the area of the wound surface, so as to change the gel area in accordance with the area of the wound surface. Finally, at the time at which the healing of the wound was completed (i.e., after three weeks in the case of the deficient wound of 2.0×2.0 cm, and after four weeks in the case of the deficient wound of 4.0×4.0 cm), the gel assumed a point-like shape or disappeared. According to the present inventor's findings, it was presumed that such a phenomenon occurred for the reason that the gel was gradually concentrated, and was discharged from the wound at the time of the completion of the wound healing.

FIGS. 2 to 5 show the results of the healing process for a wound surface obtained by naked eye observation.

Figure 2:
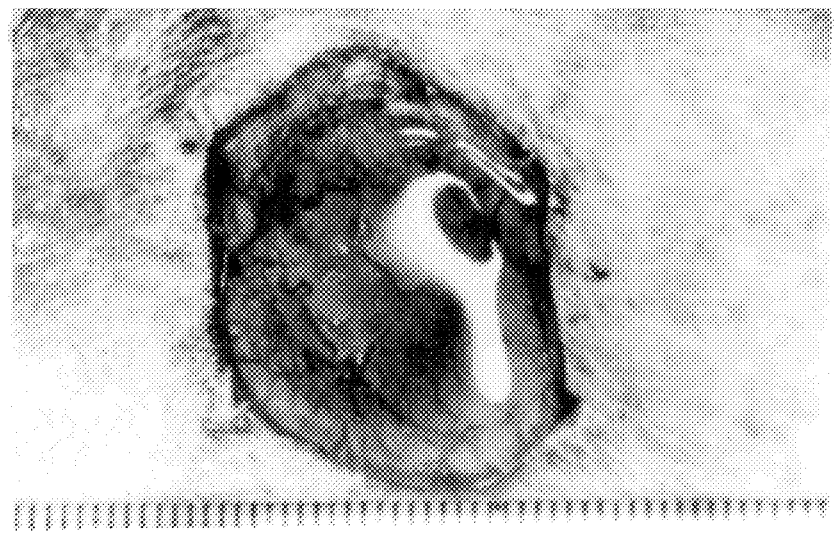
FIG. 2 is a photograph showing a state which has been obtained by forming a full-thickness skin wound having a size of 2.0×2.0 cm, pouring thereinto a solution of the above-mentioned BPE (a wound-covering material according to the present invention), converting the material into a gel state on the deficient wound, and immediately thereafter photographing the resultant state (magnification:×2.0).
Figure 3:
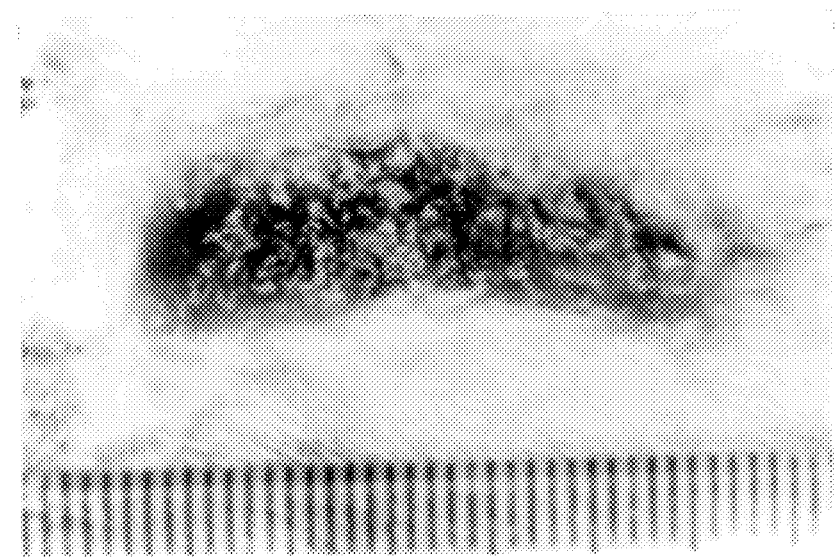
FIG. 3 is a photograph showing a state which has been obtained by forming a full-thickness skin wound having a size of 2.0×2.0 cm, placing the above BPE gel onto the deficient wound, and leaving the resultant product for one week (magnification:×2.7).
Figure 4:
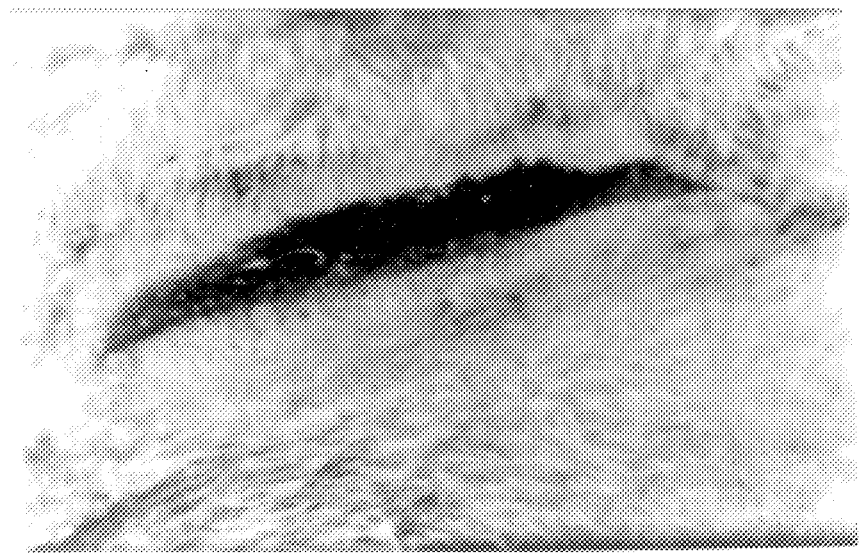
FIG. 4 is a photograph showing a state which has been obtained by forming a full-thickness skin wound having a size of 2.0×2.0 cm, placing the above BPE gel onto the deficient wound, and leaving the resultant product for two weeks (magnification:×3.8).
Figure 5:
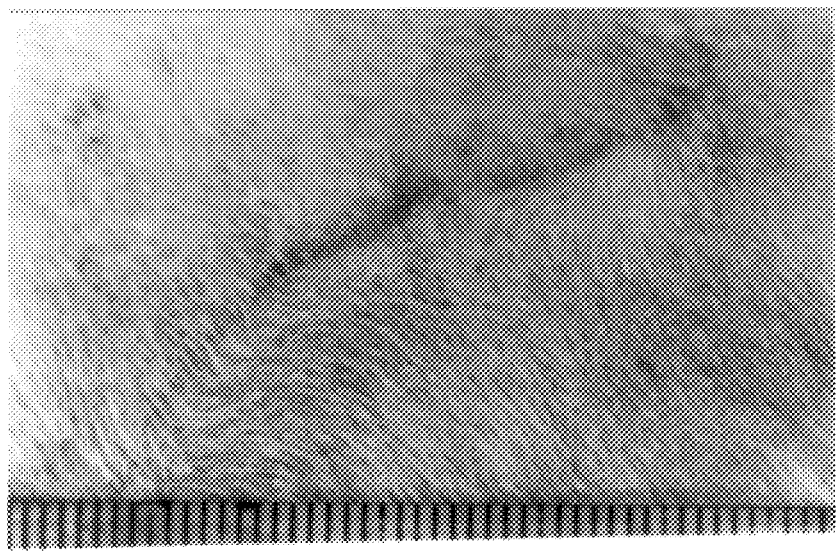
FIG. 5 is a photograph showing a state which has been obtained by forming a full-thickness skin wound having a size of 2.0×2.0 cm, placing the above BPE gel onto the deficient wound, and leaving the resultant product for three weeks (magnification:×2.4).

In the case of the deficient wound of 2.0×2.0 cm, a full-thickness skin wound was formed, the BPE solution was poured thereinto, and then converted into a gel state, and immediately thereafter, the area of the resultant wound surface was defined as 100% (FIG. 2). One week after the gel formation, the area of the wound surface was reduced to about 50% (FIG. 3). After two weeks, the area of the wound surface became about 10% (FIG. 4), and after three weeks, the wound was converted into a linear wound so that the healing of the wound was completed (FIG. 5). Thereafter, the linear wound further showed a reducing tendency, and substantially disappeared at 10 weeks so that the resultant wound was difficult to recognize by the naked eye.

As shown by the above FIG. 2, the BPE gel showed a good transparency, and it was possible to observe the state of the wound surface through the gel.

Figure 6:
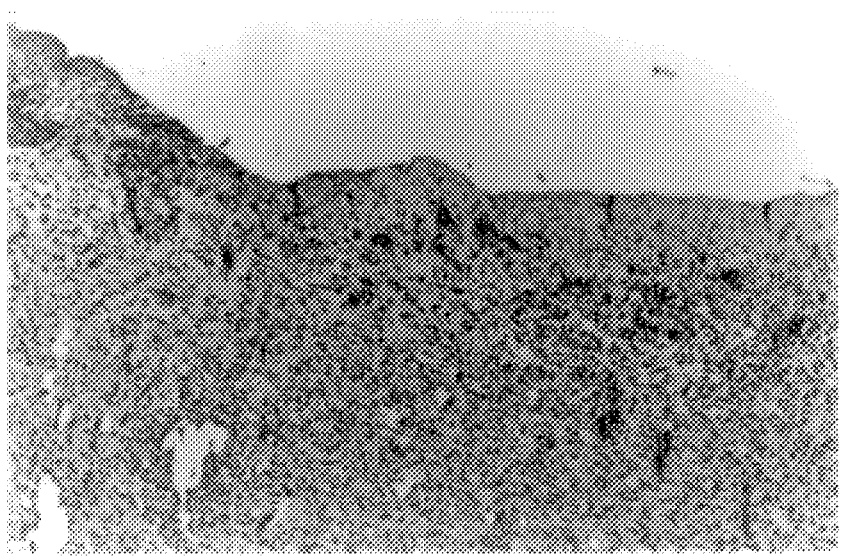
FIG. 6 is a photograph showing the histological findings of a linear wound portion, which has been obtained by placing the above BPE (a wound-covering material according to the present invention) gel on a full-thickness skin wound having a size of 2.0×2.0 cm, leaving the resultant product for three weeks, and observing a section of the linear wound (a section obtained by cutting the linear wound in a direction substantially perpendicular to the linear wound) (magnification:×78).
Figure 7:
FIG. 7 is a photograph showing the histological findings of a linear wound portion which has been obtained by placing the above BPE gel on a full-thickness skin wound having a size of 2.0×2.0 cm, leaving the resultant product for three weeks, and observing a dermis (or corium) portion of the resultant wound (magnification:×78).

FIGS. 6 to 7 show the histological findings of the above-mentioned deficient wound of 2.0×2.0 cm after three weeks. FIG. 6 shows the dermis layer of a portion of the linear wound (a section obtained by cutting the linear wound in a direction substantially perpendicular to the linear wound), and FIG. 7 shows a portion of the dermis layer which is apart from the linear wound, respectively. As shown by FIG. 6, a complete covering with epidermis was observed except at the central portion of the linear wound. In the regenerated epidermis, there had already been recognized the formation of hair follicles and sebaceous glands. In the dermis layer under the linear wound, fibroblasts were diffusively present, a large number of blood capillaries extending in the direction perpendicular toward the epidermis were observed, whereby it was microscopically judged that the tissue was in the course of healing.

On the other hand, as shown by FIG. 7, in the dermis layer apart from the linear wound, relatively thick wave-like bundles of collagen fibers and fibroblasts were sporadically observed so that such dermis was similar to the normal dermis. In the histological findings after five weeks, the regenerated epidermis could not be distinguished from normal epidermis at all. Even in the dermis layer under the linear wound, wave-like bundles of collagen fibers, a few fibroblasts, and blood capillaries were observed so that it was similar to the normal dermis.

FIGS. 8 to 12 show the results of the healing process for the surface of a wound of 4.0×4.0 cm obtained by naked eye observation. In this case, a full-thickness skin wound was formed, the BPE solution was poured thereinto, and then converted into a gel state, and immediately thereafter, the area of the resultant wound surface was defined as 100%

Figure 8:
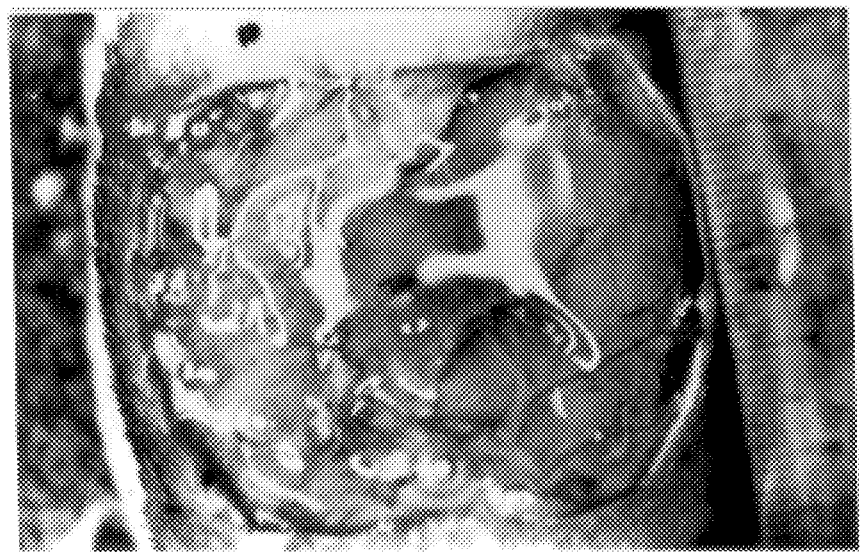
FIG. 8 is a photograph showing a state which has been obtained by pouring a solution of the above-mentioned BPE (a wound-covering material according to the present invention) into a full-thickness skin wound having a size of 4.0×4.0 cm, converting the material into a gel state on the deficient wound, and immediately thereafter photographing the resultant state (magnification:×1.5).
Figure 9:
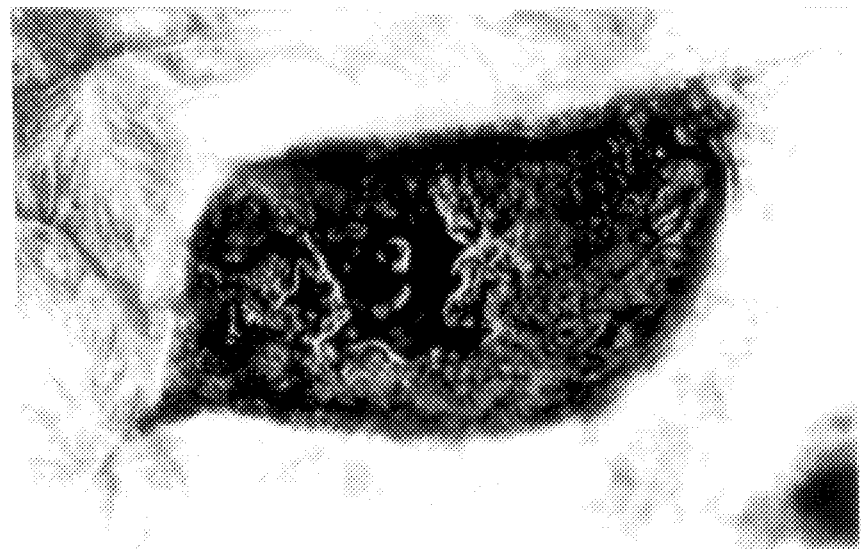
FIG. 9 is a photograph showing a state which has been obtained by pouring the above-mentioned BPE solution into a full-thickness skin wound having a size of 4.0×4.0 cm, converting the material into a gel state on the deficient wound, and leaving the resultant product for one week (magnification:×2.4).
Figure 10:
FIG. 10 is a photograph showing a state which has been obtained by pouring the above-mentioned BPE solution into a full-thickness skin wound having a size of 4.0×4.0 cm, converting the material into a gel state on the deficient wound, and leaving the resultant product for two weeks (magnification:×2.3).
Figure 11:
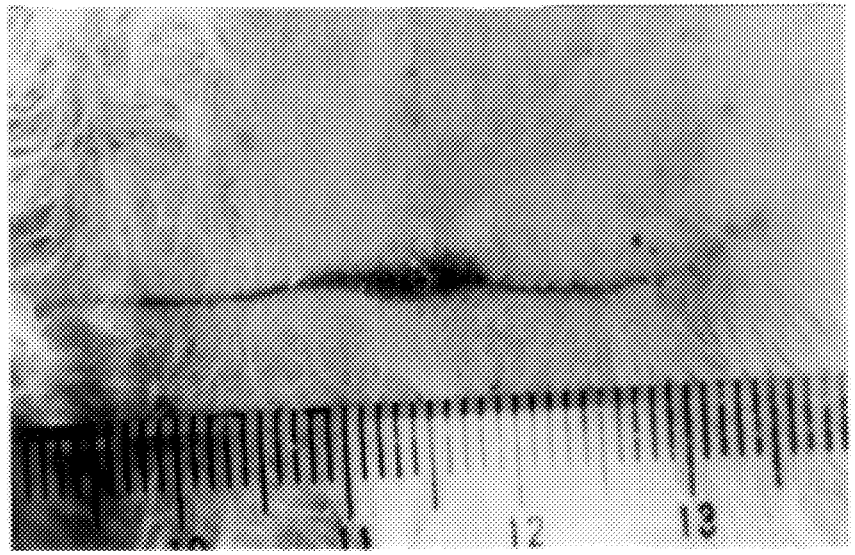
FIG. 11 is a photograph showing a state which has been obtained by pouring the above-mentioned BPE solution into a full-thickness skin wound having a size of 4.0×4.0 cm, converting the material into a gel state on the deficient wound, and leaving the resultant product for three weeks (magnification:×2.3).
Figure 12:
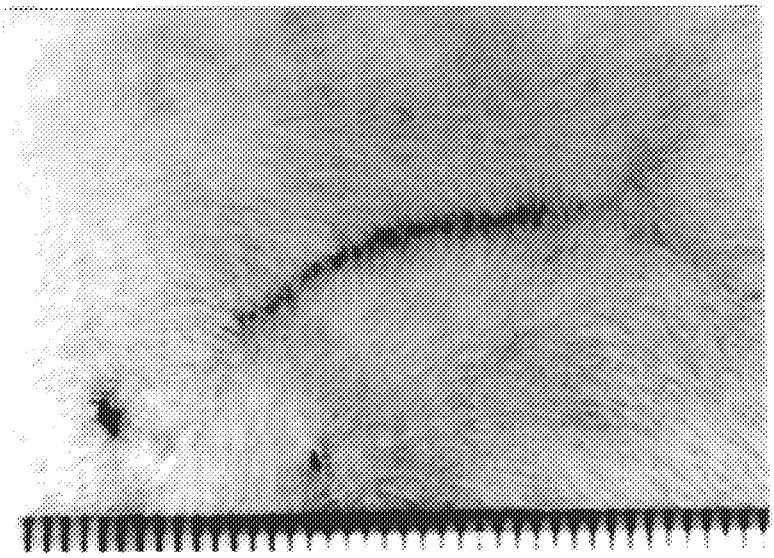
FIG. 12 is a photograph showing a state which has been obtained by pouring the above-mentioned BPE solution into a full-thickness skin wound having a size of 4.0×4.0 cm, converting the material into a gel state on the deficient wound, and leaving the resultant product for four weeks (magnification:×2.5).

(FIG. 8). One week after the gel formation, the area of the wound surface was reduced to about 60% (FIG. 9). After two weeks, the area of the wound surface became about 10% (FIG. 10), and after three weeks, the area of the wound surface became about 1% (FIG. 11), and then the wound was converted into a linear wound so that the healing of the wound was completed (FIG. 12) after four weeks. In the histological findings thereof, the observation results after four weeks were similar to those after three weeks in the case of the wound deficient of 2.0×2.0 cm. Thereafter, the observation results of this case were similar to those in the case of the wound deficient of 2.0×2.0 cm, after a delay of one week therebetween.

EXAMPLE 5

A full-thickness skin wound having a size of 4.0×4.0 cm was formed in several rats in the same manner as in Example 4. Then, the wound-covering material (GYM) synthesized in Example 2 was dissolved in a culture medium (RPMI-1640, mfd. by Nissui Seiyaku K.K.) under cooling with ice so as to provide a concentration of 5%, and thereafter the resultant mixture was sterilized by means of an autoclave (121° C., 15 min.), and then was again dissolved in the culture medium under cooling with ice.

The resultant culture medium solution of GYM cooled to 10° C. was sucked in a cooled pipet and was poured onto the surface of the above-mentioned full-thickness skin wound. The amount of the thus poured GYM solution was about 3 ml. After pouring of the above GYM solution, the GYM solution was immediately converted into a gel state on the wound surface, to thereby provide a wound-covering matter which comprised the GYM gel and was closely attached to the wound surface. Then, the outer surface of the gel was covered with a 1 mm-thick transparent polyurethane film for the purpose of protecting the wound surface covered with the GYM gel, and to maintain the wetted state of the GYM gel. Thereafter, the outer surface of the transparent polyurethane film was bandaged under pressure by means of an Elastoband.

In the same manner as in Example 4, with the elapse of time, the gel state of the thus covered GYM gel was observed with the naked eye, and the presence or absence of the accumulation of exudate from the wound surface was observed. Further, the area of the wound surface was measured by taking photographs thereof at intervals of one week. Within the period of time during which the above observation was conducted, no accumulation of exudate between the GYM gel and the wound surface was observed, the gel did not float above the wound surface and flow away, and did not dissolve and disappear, but the GYM gel completely covered the wound surface in close contact. The process of the healing of the wound surface covered with the gel was substantially the same as that in the case of the BPE gel in Example 4, and the healing of the wound was completed after four weeks. In this case using the GYM gel, similar to the case of the BPE gel, the GYM gel increased its gel strength along with the decrease in the area of the wound surface so as to change the gel area in accordance with the area of the wound surface. Finally, at the time at which the healing of the wound was completed, the gel was discharged from the wound. In addition, when the histological findings of the wound surface covered with the GYM gel were performed, it was found that the histological findings were substantially the same as that in the case of the BPE gel.

EXAMPLE 6

Experiments of healing mouse wounds were conducted in the same manner as in Example 4 except that the thickness of the transparent polyurethane film used in Example 4 was changed to 30 μm. As a result, it was found that, one week after the wound-covering matter in a gel form was formed on the wound surface, there was a tendency to provide a clearance between the gel and the wound surface due to the shrinkage of the gel based on the drying thereof. In a case where such a clearance occurred, there were sometimes observed an example wherein exudate was accumulated in the above-mentioned clearance so as to cause infection; and an example wherein the gel was cracked due to drying thereof so that the fragments of the gel were incorporated into the tissue.

Comparative Example 1

A full-thickness skin wound of 2.0×2.0 cm or 4.0×4.0 cm was formed on each of several rats in the same manner as in Example 4, and thereafter comparative experiments were conducted while leaving the above wounds open.

In the case of the deficient wound of 2.0×2.0 cm, the shrinkage of the wound was caused and regenerated epidermis was formed. After three weeks, the closure of the wound was recognized, but cicatricial wounds having a size corresponding to an adzuki bean was recognized, and therefore the resultant shape thereof was not good. Histologically, it was recognized that the above-mentioned deficient wound was substituted with dermal cicatricial tissue, and no position thereof was similar to the normal dermis. The resultant epidermis was thickened and became hyperplasia, and no hair follicle nor sebaceous gland therein was observed.

On the other hand, in the case of the deficient wound of 4.0×4.0 cm, the wound was rapidly shrunk over three weeks so as to reduce the area of the wound surface. However, shrinkage thereof did not occur thereafter, and a cicatricial wound having an ugly mark remained. The histological findings was the same as that in the case of the deficient wound of 2.0×2.0 cm.

Comparative Example 2

A full-thickness skin wound having a size of 2.0 cm×2.0 cm or 4.0×4.0 cm was formed on each of several rats in the same manner as in Example 4.

Then, Pluronic F-127 (mfd. by BASF Co.) was dissolved in a physiological saline under cooling with ice so as to provide a concentration of 20%, and thereafter the resultant mixture was sterilized by means of an autoclave (121° C., 20 min.), and then was again dissolved in the physiological saline under cooling with ice. The resultant physiological saline solution of Pluronic F-127 cooled to 10° C. was sucked in a cooled pipet and was poured onto the surface of the above-mentioned full-thickness skin wound. The amount of the thus poured solution was about 1.2 ml and about 3 ml, respectively, in the cases of the deficient wounds of 2.0 cm×2.0 cm and 4.0×4.0 cm. After the pouring of the above Pluronic F-127 solution, the solution began to be converted to a gel state within several seconds, and was completely converted into a gel state after one min., to thereby provide a matter closely attached to the wound surface.

Then, in the same manner as in the cases of the BPE gel and GYM gel, the outer surface of the wound covered with the Pluronic F-127 gel was covered with a 1 mm-thick transparent polyurethane film, and thereafter, the outer surface of the transparent polyurethane film was bandaged under pressure by means of an Elastoband.

In the same manner as in Examples 4 and 5, with the elapse of time, the gel state of the thus covered wound surface was observed. As a result, when the above-mentioned Pluronic F-127 gel was placed on the wound surface for a day, it was found that the gel had already been dissolved and disappeared completely. According to the present inventor's findings, it was presumed that the gel was dissolved by the exudate secreted from the wound surface.

Even when the Pluronic F-127 solution was newly poured onto the above-mentioned wound surface, it was dissolved and extinguished one day after the new pouring, similar to the previous pouring. When such an operation was repeated, a thin film-like matter was formed on the wound surface five days after the formation of the deficient wound. However, at this time, even when the Pluronic F-127 solution was newly poured onto the above-mentioned wound surface, it did not attached to the wound surface closely, but flowed away.

In the case of the deficient wound of 2.0×2.0 cm, the shrinkage of the area of the wound surface was recognized. However, in the case of the deficient wound of 4.0×4.0 cm, the wound was not converted into a linear wound even after four weeks, but a cicatricial wound having an ugly mark remained which was similar to that observed in the case of the open wound (Comparative Example 1).

Industrial Applicability

As described hereinabove, the present invention provides a wound-covering material which may closely be attached to a wound surface having a complex profile, since it may be placed on the wound surface in a liquid state, and may rapidly be converted into a gel state so as to provide a wound-covering matter closely and stably attached to the wound surface; and the present invention also provides a wound-covering composition or wound-covering matter utilizing such a material.

As described above, the wound-covering material according to the present invention may provide a wound-covering matter which may closely be attached to a complex profile of a wound surface without leaving a clearance therebetween, and is stable without being dissolved in exudate secreted from the wound surface. Accordingly, the above wound-covering material may prevent the secretion of the exudate from the wound surface until the completion of the wound surface healing so as to provide an environment similar to that in a living organism, whereby it prevents the formation of a cicatricial wound having an ugly mark, and simultaneously, remarkably promotes the process of the wound healing, unlike the conventional wound-covering mediums in the prior art.

In addition, a gel based on the wound-covering material according to the present invention may change its dimension (or size) and strength in accordance with the shrinkage of the wound surface, whereby the gel may automatically be discharged from the living organism at the time of the completion of the wound healing.

I claim:

1. A wound-covering material comprising a polymer having a sol-gel transition temperature in an aqueous solution, a substantial water-insolubility at a temperature higher than the sol-gel transition temperature, and a reversible water-solubility at a temperature lower than the sol-gel transition temperature, said polymer being capable of providing a thermally reversible gel that is substantially insoluble in water at a temperature higher than the sol-gel transition temperature, the gel of said wound-covering material having a water-insolubility such that the gel exhibits a weight decrease of 5.0% or less when the gel is left standing in water at 37° C. for 10 hours.

2. The wound-covering material according to claim 1, wherein the polymer is a polymer comprising a plurality of blocks having a cloud point, and a hydrophilic block combined therewith.

3. The wound-covering material according to claim 1, wherein the sol-gel transition temperature is higher than 0° C. and is not higher than 40° C.

4. The wound-covering material according to claim 1, which further comprises an antibacterial agent.

5. The wound-covering material according to claim 1, which further comprises a wound healing-accelerator.

6. A wound-covering composition comprising, at least, water and a polymer having a sol-gel transition temperature in an aqueous solution thereof, a liquid state (sol state) at a temperature lower than the sol-gel transition temperature, and a thermally reversible gel state comprising a gel which is substantially water-insoluble at a temperature higher than the sol-gel transition temperature, the gel of said wound-covering composition having a water-insolubility such that the gel exhibits a weight decrease of 5.0% or less, when the gel is left standing in water at 37° C. for 10 hours.

7. The wound-covering composition according to claim 6, which is capable of again assuming a liquid state (sol state), by once converting it into a gel state, and then lowering the temperature to lower than the sol-gel transition temperature.

8. The wound-covering composition according to claim 6, wherein the polymer is a polymer comprising a plurality of blocks having a cloud point, and a hydrophilic block combined therewith.

9. The wound-covering composition according to claim 6, wherein the sol-gel transition temperature is higher than 0° C. and is not higher than 40° C.

10. The wound-covering composition according to claim 6, which further comprises an antibacterial agent.

11. The wound-covering composition according to claim 6, which further comprises a wound healing-accelerator.

12. A wound-covering medium, comprising a layer of a composition to be placed on the side of a wound, and a membrane having a low water vapor permeability disposed on the outside of the composition layer; the composition layer comprising, at least, water and a polymer having a sol-gel transition temperature in an aqueous solution, a liquid state (sol state) at a temperature lower than the sol-gel transition temperature, and a gel state comprising a gel which is substantially water-insoluble at a temperature higher than the sol-gel transition temperature, the gel of said composition layer having a water-insolubility such that the gel shows a weight decrease of 5.0% or less, when the gel is left standing in water at 37° C. for 10 hours.

13. The wound-covering medium according to claim 12, which is capable of again assuming a liquid state (sol state), by once converting it into a gel state, and then lowering the temperature to lower than the sol-gel transition temperature.

14. The wound-covering medium according to claim 12, wherein the polymer is a polymer comprising a plurality of blocks having a cloud point, and a hydrophilic block combined therewith.

15. The wound-covering medium according to claim 12, wherein the sol-gel transition temperature is higher than 0° C. and is not higher than 40° C.

16. The wound-covering medium according to claim 12, which further comprises an antibacterial agent.

17. The wound-covering medium according to claim 12, which further comprises a wound healing-accelerator.

* * * * *